United States Patent [19]

Myers

[11] 3,947,438

[45] Mar. 30, 1976

[54] DECARBONYLATION OF QUINOXALINES
[75] Inventor: Robert F. Myers, East Lyme, Conn.
[73] Assignee: Pfizer Inc., New York, N.Y.
[22] Filed: Oct. 15, 1974
[21] Appl. No.: 514,451

[52] U.S. Cl......... 260/250 QN; 424/250; 260/307 D
[51] Int. Cl.².......................................... C07D 241/52
[58] Field of Search.................. 260/250 Q, 250 QN

[56]         References Cited
         UNITED STATES PATENTS
3,493,572   2/1970   Johnston...................... 260/250 QN Primary Examiner—Alton D. Rollins
Attorney, Agent, or Firm—Connolly and Hutz

[57]            ABSTRACT

Designated 2-formylquinoxaline 1,4-dioxides are decarbonylated by the action of an unhindered secondary amine having a $pK_a$ greater than about 8 to produce the corresponding decarbonylated product.

6 Claims, No Drawings

DECARBONYLATION OF QUINOXALINES

The present invention relates to decarbonylation, more particularly to the decarbonylating of aldehydes having the 2-formylquinoxaline 1,4-dioxide structure.

Among the objects of the present invention is the provision of a novel decarbonylating process that is simple to carry out and yet quite effective.

These as well as additional objects of the present invention will be more fully understood from the following description of several of its exemplifications.

The decarbonylation of the present invention is carried out by subjecting an aldehyde having the formula

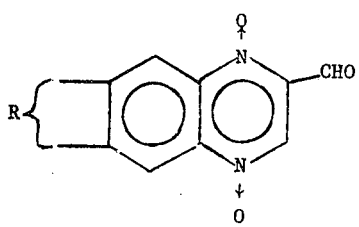

in liquid condition to the action of at least an equivalent amount of an unhindered secondary amine having a $pK_a$ greater than about 8 at a temperature of from about 30° to about 150°C., to decarbonylate the CHO group and form the corresponding decarbonylated product.

In the above formula R is in either of the indicated (6- and 7-) positions, and it is hydrogen, hydrocarbyl having up to four carbons, alkylthio having up to four carbons, alkylsulfinyl having up to four carbons, alkylsulfonyl having up to four carbons, fluoro, chloro, bromo, iodo, cyano, trifluoromethyl, alkanoyl having up to four carbons, $CONR^1R^2$ or $SO_2NR^1R^2$, $R^1$ and $R^2$ being separately selected from the class consisting of hydrogen and alkyl having up to three carbons.

The foregoing 2-formylquinoxaline 1,4-dioxides are either known compounds or they are readily prepared by standard methods, well-known to those skilled in the art. For example, the compounds wherein R is hydrogen, hydrocarbyl, alkoxy, alkylthio, fluoro, chloro, bromo, iodo, trifluoromethyl, alkanoyl, $CONR^1R^2$ or $SO_2NR^1R^2$ are prepared by reaction of the appropriate benzofurazan 1-oxide with pyruvaldehyde dimethyl acetal, followed by hydrolysis of the acetal grouping, according to the methods described in Example XXXIX of British Pat. Spec. No. 1,215,815. The compounds wherein R is alkylsulfinyl or alkylsulfonyl are prepared by reaction of the appropriate alkylthio-substituted benzofurazan 1-oxide with pyruvaldehyde dimethyl acetal, followed by oxidation of the alkylthio moiety either to an alkylsulfinyl or an alkylsulfonyl group, followed by hydrolysis of the acetal grouping. A convenient reagent useful for the latter oxidation step is a peracid, such as m-chloroperbenzoic acid.

The above-mentioned benzofurazan 1-oxides appear to exist as dynamic tautomeric mixtures, containing both the 5- and 6-isomers. When these compounds are converted into quinoxaline 1,4-dioxides, the latter appear to be a mixture of the 6- and 7-isomers, and for this reason the parenthetical "7" is included in the names of these compounds. In the decarbonylated products, the 6- and 7- positions are identical, and only a single product is formed.

The secondary amines that effect the decarbonylation have their amine nitrogen bonded to two different carbon atoms and to a hydrogen. They are also unhindered in that the two carbon atoms to which the foregoing nitrogen is bonded each have no more than one substituent larger than hydrogen. Preferably each of those carbons carries two hydrogens and an additional alkyl with one to three carbons. These alkyl can also be bonded to each other to form an alkylene or similar bridge from one of the nitrogen-bonded carbons to the other.

Amines that are not strongly nucleophilic are not desirable reactants, and as a class they should have a $pK_a$ greater than about 8. Typical preferred amines are piperidine, diethylamine, dimethylamine, di-n-propylamine, morpholine, thiomorpholine, N-methylbenzylamines and 1,2,3,4-tetrahydroisoquinoline. An aromatic ring such as benzene ring, when bonded to the amine nitrogen diminishes the nucleophilic character too much, as does a heavy inactive structure such as alkyl of over twenty carbons. Various other substituents can be present in the amine including hydroxy groups or other secondary or tertiary amine functions. Typical examples of these latter types are N-methylethanolamine, diethanolamine, N,N'-dimethylethylenediamine, N,N',N'-trimethylethylenediamine and N-methylpiperazine.

As is well known by those skilled in the art, the $pK_a$ value of an amine is a measure of the acidity of its conjugate acid, i.e., its protonated form. Lists of such values, as well as techniques for determining them, are well documented. See, for example, "Constants of Organic Compounds," Munio Kotake editor, Asakura Publishing Company, Ltd., Osaka, Japan, 1963, page 584 et seq; and "Handbook of Chemistry and Physics," 51st edition, 1970–1971, Robert C. Weast editor, The Chemical Rubber Co., Cleveland, Ohio, pages D117 to D119.

The decarbonylation of the present invention proceeds too slowly or stops altogether, at temperatures below 30°C. Temperatures above 150°C are not desired because they tend to excessively reduce the yields. Preferred temperatures are from about 50° to 100°C.

Subjecting the above-mentioned aldehydes to the decarbonylating action of the designated secondary amines is not very effective when either or both of these reactants are in solid form. The reaction is however quite efficient when both are in liquid form. The designated secondary amines are generally liquid at temperatures of 50°C or higher, and some are gaseous but can be kept in liquid condition by holding them under pressure and/or dissolving them in a higher boiling solvent. The designated amines can be used alone, without the addition of a further diluent, but the solubilities are generally so small that a large excess of amine would be needed to completely dissolve the aldehyde even at 100°C.

The decarbonylation reaction seems to be of noncatalytic nature, and equimolar amounts of the reactants react to provide yields as high as 70% after a few hours at 65°C. A molar proportion of the designated secondary amine at least half that of the aldehyde gives good results, and if desired the reaction can be carried out in stages with the reacting amine added in successive portions at spaced intervals. An excess of 100 or 200% of the reacting amine can also be used very efficiently, but the excess is then little more than added solvent, and it is generally preferred that the solvent be a low viscosity liquid in which the decarbonylated product is not very soluble and from which it can be readily filtered and washed. A low boiling solvent such as methanol is also advantageous in that not only is it of low viscosity, but the reaction can be readily conducted in it at reflux with a minimum of attention, and it can be readily removed by vacuum stripping or the like. The reacting aldehyde is generally much more costly than the reacting amine so that it is preferred to have at least an equimolar amount of the amine and thus make sure there is no significant waste of the aldehyde.

Mixtures of solvents are also very effective, and a little water can be present in the solvents so long as it does not render the reactants too insoluble. A perfect solution is not needed for effective decarbonylation, and aldehyde can remain undissolved, if it is in finely divided form, without significantly detracting from the reaction effectiveness.

The time course of the reaction varies according to a number of factors, such as the reactivity and concentration of the reactants, and the reaction temperature. As will be appreciated by one skilled in the art, the reaction proceeds faster at higher temperatures and relatively short reaction times are used; whereas at lower temperatures the reaction proceeds more slowly and longer reaction times are required, in order to obtain a good yield of product. Having full regard for these factors, when working at the preferred temperature, reaction times of several hours, for example from about one hour to about twenty-four hours are typically used. With the more nucleophilic of the reacting amines there will generally be some reaction product formed within the first few minutes of reaction, and such product will also generally precipitate and can be removed from the reaction mixture as it is formed, with or without interruption of the reaction. It is not desirable to have so much solvent that the aldehyde content is initially below about 1% in concentration, by weight.

The decarbonylated product is generally much less soluble in the reaction mixture than the starting aldehyde, and in many cases will spontaneously precipitate during the course of the reaction or after the reaction is completed and the reaction mixture cooled to room temperature.

Recovery of the decarbonylated product is readily effected. For example, in those instances where the product precipitates during the course of the reaction, it can be recovered simply by filtration. Alternatively, when the product does not precipitate spontaneously, it can often be induced to precipitate at the end of the reaction by dilution of the reaction medium with a non-solvent, such as hexane or water. A further method of product recovery involves removal of the solvents by evaporation followed by acidification of the crude product and extraction with water. Where the reacting amine is water-soluble it can also be removed by partitioning the crude product, with or without a stripping, between water and a water-immiscible organic solvent. After separation of the two phases, the product-containing organic phase is evaporated to yield the product.

The following examples are typical of the decarbonylation of the present invention.

EXAMPLE I

Decarbonylation of 2-Formylquinoxaline 1,4-Dioxide with Piperidine

To a stirred slurry of 10.0 g. (0.053 mole) of 2-formylquinoxaline 1,4-dioxide in 100 ml. of methanol is added 4.5 g. (0.053 mole) of piperidine. This causes the mixture to warm up and form an almost complete solution containing a little suspended solid, following which a yellow precipitate begins to form. The mixture is then heated under reflux (about 70°C.) for 3 hours. At this point, examination of the reaction mixture by thin-layer chromatography still reveals the presence of a little starting aldehyde. A further 2.25g. (0.027 mole) of piperidine is added and the reaction mixture is heated under reflux for a further 2.5 hours at which time only a trace of starting aldehyde is shown by thin-layer chromatography. The mixture is then cooled to ambient temperature and the solid which precipitates is filtered off. This affords 6.0g. (70% yield) of quinoxaline 1,4-dioxide, mp 245°–247°C. The nuclear magnetic resonance spectrum of the product shows absorptions at 9.05 ppm (singlet, 2H), 8.85 ppm (multiplet, 2H) and 8.20 ppm (multiplet, 2H), downfield from tetramethylsilane.

The thin-layer chromatography works well when using a mixture of 5 parts chloroform to 1 part ethanol, by volume.

EXAMPLE II

Decarbonylation of 6(7)-Methyl-2-formylquinoxaline 1,4-Dioxide with Piperidine

To a stirred suspension of 1.0g. (0.0049 mole) of 6(7)-methyl-2-formylquinoxaline 1,4-dioxide in 10 ml. of methanol is added 0.733 ml. (0.00735 mole) of piperidine and then the mixture is heated slowly to reflux. During this heat-up all of the suspended material dissolves. The reaction mixture is maintained at reflux temperature for an additional 2 hours, and then it is cooled to ambient temperature. The solid which precipitates is filtered off, giving 0.55g. (64% yield) of 6-methylquinoxaline, mp. 215°–216°C. The nuclear magnetic resonance spectrum of the product shows absorptions at 8.5 – 7.4 ppm (multiplet, 5H) and 2.6 ppm (singlet, 3H), downfield from tetramethylsilane; the infrared spectrum of the product confirms the absence of a carbonyl group; the product shows a single spot when examined by thin-layer chromatography; and its C H and N analyses confirm it as $C_9H_8O_2N_2$.

A second crop (0.125g.) of product is obtained by heating the filtered reaction mixture for an additional 3 hours, bringing the total yield to 0.675g. (79% yield).

EXAMPLE III

The procedure of Example II is repeated except that the 6(7)-methyl-2-formylquinoxaline 1,4-dioxide used therein is replaced by an equimolar amount of
6(7)-ethyl-2-formylquinoxaline 1,4-dioxide,
6(7)-isopropyl-2-formylquinoxaline 1,4-dioxide,
6(7)-n-butyl-2-formylquinoxaline 1,4-dioxide,
6,7-dimethyl-2-formylquinoxaline 1,4-dioxide,
6(7)-methoxy-2-formylquinoxaline 1,4-dioxide,
6(7)-isobutoxy-2-formylquinoxaline 1,4-dioxide,
6(7)-methylthio-2-formylquinoxaline 1,4-dioxide,
6(7)-n-butylthio-2-formylquinoxaline 1,4-dioxide,
6(7)-methylsulfinyl-2-formylquinoxaline 1,4-dioxide, 6(7)-isopropylsulfinyl-2-formylquinoxaline 1,4-dioxide,
6(7)-methylsulfonyl-2-formylquinoxaline 1,4-dioxide,
6(7)-isobutylsulfonyl-2-formylquinoxaline 1,4-dioxide,
6(7)-cyano-2-formylquinoxaline 1,4-dioxide,
6(7)-bromo-2-formylquinoxaline 1,4-dioxide,
6(7)-chloro-2-formylquinoxaline 1,4-dioxide,
6(7)-fluoro-2-formylquinoxaline 1,4-dioxide,
6(7)-trifluoromethyl-2-formylquinoxaline 1,4-dioxide,
6(7)-[N-propylsulfonamido]-2-formylquinoxaline 1,4-dioxide and
6(7)-[N,N-dimethylsulfonamide]-2-formylquinoxaline 1,4-dioxide,
respectively. There is recovered from these reactions
6-ethylquinoxaline 1,4-dioxide,
6-isopropylquinoxaline 1,4-dioxide,
6-n-butylquinoxaline 1,4-dioxide,
6,7-dimethylquinoxaline 1,4-dioxide
6-methoxyquinoxaline 1,4-dioxide,
6-isobutoxyquinoxaline 1,4-dioxide,
6-methylthioquinoxaline 1,4-dioxide,
6-n-butylthioquinoxaline 1,4-dioxide,
6-methylsulfinylquinoxaline 1,4-dioxide,
6-isopropylsulfinylquinoxaline 1,4-dioxide,
6-methylsulfonylquinoxaline 1,4-dioxide,
6-isobutylsulfonyl
6-cyanoquinoxaline 1,4-dioxide,
6-bromoquinoxaline 1,4-dioxide,
6-chloroquinoxaline 1,4-dioxide,
6-fluoroquinoxaline 1,4-dioxide,
6-trifluoromethylquinoxaline 1,4-dioxide,
6-[N-propylsulfonamide]quinoxaline 1,4-dioxide, and
6-[N,N-dimethylsulfonamide] quinoxaline 1,4-dioxide,
respectively.

Mixtures of the foregoing aldehydes are also decarbonylated in accordance with the present invention, including mixtures having two different "R" substituents. It is likewise unnecessary for the aldehydes to be in highly purified form, and the same is true for the amines.

EXAMPLE IV

Decarbonylation of 6(7)-Methoxy-2-formylquinoxaline 1,4-Dioxide with N-Methyl-N-(2-hydroxyethyl)amine A mixture of 2.20g. of 6(7)-methoxy-2-formylquinoxaline 1,4-dioxide and 750 mg. of N-methyl-N-(2-hydroxyethyl)amine in 30 ml. of ethanol is heated under reflux for 4 hours, and the mixture then cooled to 25°C. The solvent is removed from the resulting mixture by evaporation in vacuo, and the residue washed with ether and dried, to yield crude 6-methoxyquinoxaline 1,4-dioxide, which can be purified further by recrystallization from chloroform, if desired.

EXAMPLE V

The procedure of Example IV is repeated, except that the N-methyl-N-(2-hydroxyethyl)amine used therein is replaced by an equimolar amount of:
Pyrrolidine
N,N-di(n-butyl)amine,
N-isopentyl-N-methylamine,
N-ethyl-N-n-octylamine,
N-n-decyl-N-methylamine,
N,N-diallylamine,
N-cyclohexyl-N-(3-methyl-2-butenyl)amine,
N-methyl-N-(2-octenyl)amine,
N-methyl-N-(2-decenyl)amine,
N-benzyl-N-(3-hydroxypropyl)amine,
N-methyl-N-4-hydroxybutyl)amine,
N-(2-butoxyethyl)-N-methylamine,
N-(4-methoxybutyl)-N-ethylamine,
N,N'-dimethylethylenediamine,
N-(3-[ethylamino]propyl)-N-n-propylamine.
N-(5-[ethylamino]pentyl)-N-benzylamine,
N,N,N'-trimethylethylenediamine,
N,N,N,'-triethylethylenediamine,
N-(5-[diethylamino]pentyl)-N-ethylamine,
morpholine,
thiomorpholine,
piperazine,
N-methylpiperazine,
N-n-propylpiperazine,
N-(methoxycarbonyl)piperazine, and
N-(isopropoxycarbonyl)piperazine,
respectively. The product in each case is 6-methoxyquinoxaline 1,4-dioxide. This product is also correspondingly formed when dioxane or 2-methyl imidazole is used as solvent in place of the ethanol in each of the foregoing Example IV modifications.

EXAMPLE VI

5-Cyanobenzofurazan 1-Oxide

A stirred solution of 48.0 g. (0.263 mole) of 4-chloro-3-nitrobenzonitrile (Le Fevre and Turner, J. Chem. Soc., London,1113[1927]) in 360 ml. of dimethyl sulfoxide is treated portionwise, at ambient temperature, with 17.0 g. (0.263 mole) of sodium azide. The resulting solution is stirred overnight at ambient temperature, and then it is poured into 2,400 ml. of water. The aqueous solution thus obtained is extracted with 1,000 ml. of ethyl acetate, and the organic extract is washed with water and then dried using anhydrous sodium sulfate. The dried solution is concentrated to about half volume, in vacuo, and then it is heated under reflux for 3 hours. At this point, the ethyl acetate solution is cooled to ambient temperature. Removal of the remaining solvent by evaporation in vacuo affords 41.2 g. (97% yield) of 5-cyanobenzofurazan 1-oxide, m.p. 73°–76°C.

Analysis-Calc'd for $C_7H_3N_3O_2$ (percent): C, 52.2; H, 1.9; N, 26.1. Found (percent): C, 52.1; H, 2.3; N, 25.8.

The other benzofurazan 1-oxides used to form the aldehydes decarbonylated in accordance with the present invention are either known compounds, or they are prepared by well-known methods. See, for instance, *Organic Syntheses*, Collective Volume IV, John Wiley & Sons, Inc. New York-London, 1963, pages 74 to 78.

The quinoxaline dioxides produced by the decarbonylation of the present invention can be recovered in yields that are better and purer than available through other routes such as described in U.S. Pat. No. 3,660,398 or by direct oxidation of the corresponding quinoxaline. The final products are useful as antibacterial agents, as antiviral agents, and as animal growth promoters. Details of some uses in these respects are given by King et al in Journal of the Chemical Society, London, beginning at page 3012 of the 1949 volume, by Hurst et al in British Journal of Pharmacology Volume 8, beginning at page 297 (1953), and by British Patent Specifications Nos. 1,215,815, 1,223,720 and 1,308,370.

Obviously many modifications and variations of the present invention are possible in the light of the above teachings. It is, therefore, to be understood that within the scope of the appended claims the invention may be practiced otherwise than as specifically described.

What is claimed:

1. A process which comprises subjecting an aldehyde having the formula

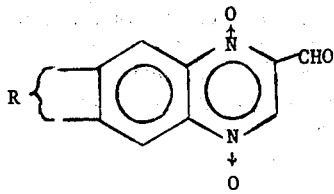

where
R is in either of the indicated positions and is hydrogen, alkyl, having up to four carbons, alkoxy having up to four carbons, alkylthio having up to four carbons, alkylsulfinyl having up to four carbons, alkylsulfonyl having up to four carbons, fluoro, chloro, bromo, cyano, trifluoromethyl, alkanoyl having two to four carbons, $CONR^1R^2$ or $SO_2NR^1R^2$, $R^1$ and $R^2$ being separately selected from the class consisting of hydrogen and alkyl having up to three carbons,
in liquid condition to the action of at least 0.5 molar equivalents of an unhindered secondary amine having a $pK_a$ greater than about 8, at a temperature of from about 30° to about 150°C., to decarbonylate the CHO group and form the corresponding decarbonylated product.

2. The process of claim 1 in which the action is effected at from about 50° to about 100°C.

3. The process of claim 1 in which the secondary amine is piperidine.

4. The process of claim 1 in which R is hydrogen.

5. The process of claim 1 in which the action is effected in a solvent in which the aldehyde is dissolved.

6. The process of claim 1 in which at least one molar equivalent of amine is used.

* * * * *